United States Patent
Craig

(10) Patent No.: US 8,617,157 B2
(45) Date of Patent: Dec. 31, 2013

(54) HERNIA REPAIR SYSTEM

(75) Inventor: Jason L. Craig, Loveland, CO (US)

(73) Assignee: Covidien LP, Mansfield, MA (US)

( * ) Notice: Subject to any disclaimer, the term of this patent is extended or adjusted under 35 U.S.C. 154(b) by 874 days.

(21) Appl. No.: 12/693,986

(22) Filed: Jan. 26, 2010

(65) Prior Publication Data
US 2011/0184407 A1 Jul. 28, 2011

(51) Int. Cl.
*A61B 18/18* (2006.01)

(52) U.S. Cl.
USPC ............................................. 606/41; 606/151

(58) Field of Classification Search
USPC ......................................... 606/151, 154, 41
See application file for complete search history.

(56) References Cited

U.S. PATENT DOCUMENTS

| | | | |
|---|---|---|---|
| 5,292,362 A | 3/1994 | Bass et al. | |
| 5,470,010 A | 11/1995 | Rothfuss et al. | |
| 5,824,015 A * | 10/1998 | Sawyer | 606/214 |
| 5,972,007 A * | 10/1999 | Sheffield et al. | 606/151 |
| 6,004,333 A * | 12/1999 | Sheffield et al. | 606/151 |
| 6,251,110 B1 | 6/2001 | Wampler | |
| 6,287,344 B1 * | 9/2001 | Wampler et al. | 623/23.72 |
| 7,044,982 B2 * | 5/2006 | Milbocker | 623/23.72 |
| 7,160,299 B2 | 1/2007 | Baily | |
| 7,186,251 B2 * | 3/2007 | Malecki et al. | 606/41 |
| 2003/0212395 A1 | 11/2003 | Woloszko et al. | |
| 2007/0112361 A1 * | 5/2007 | Schonholz et al. | 606/151 |
| 2007/0185541 A1 * | 8/2007 | DiUbaldi et al. | 607/41 |
| 2007/0293878 A1 * | 12/2007 | Butsch | 606/151 |
| 2008/0058798 A1 | 3/2008 | Wallace et al. | |
| 2009/0192528 A1 * | 7/2009 | Higgins et al. | 606/151 |
| 2010/0114126 A1 * | 5/2010 | Neff | 606/151 |
| 2010/0292718 A1 * | 11/2010 | Sholev et al. | 606/151 |
| 2010/0298953 A1 * | 11/2010 | Holzman | 623/23.72 |
| 2011/0184440 A1 * | 7/2011 | Saldinger | 606/151 |
| 2011/0238094 A1 * | 9/2011 | Thomas et al. | 606/151 |

FOREIGN PATENT DOCUMENTS

| | | | |
|---|---|---|---|
| WO | WO 2007/056297 A2 | 5/2007 | |
| WO | WO 2009/011824 A1 | 1/2009 | |

OTHER PUBLICATIONS

European Search Report for EP 11 25 0084 application, date of completion, Jun. 21, 2011.

* cited by examiner

*Primary Examiner* — Linda Dvorak
*Assistant Examiner* — Jocelyn D Ram

(57) ABSTRACT

A hernia repair system includes a surgical mesh, one or more electrosurgical instruments, and one or more return electrodes. The one or more electrosurgical instruments are configured to position the surgical mesh adjacent tissue in an underlying tissue site. The one or more return electrodes are positionable adjacent the tissue and externally relative to the underlying tissue site. The one or more electrosurgical instruments and the one or more return electrodes are configured to selectively apply an effective amount of pressure and electrosurgical energy to the surgical mesh such that upon the application of electrosurgical energy and pressure, the surgical mesh seals to one side of the tissue at the underlying tissue site.

14 Claims, 5 Drawing Sheets

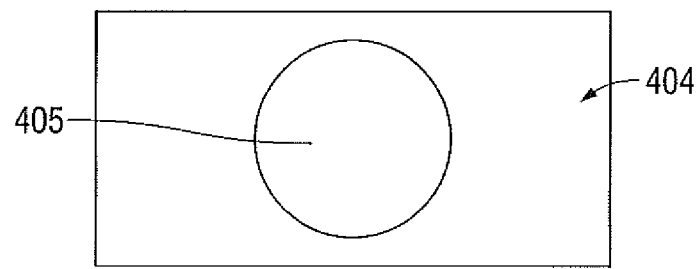
FIG. 7
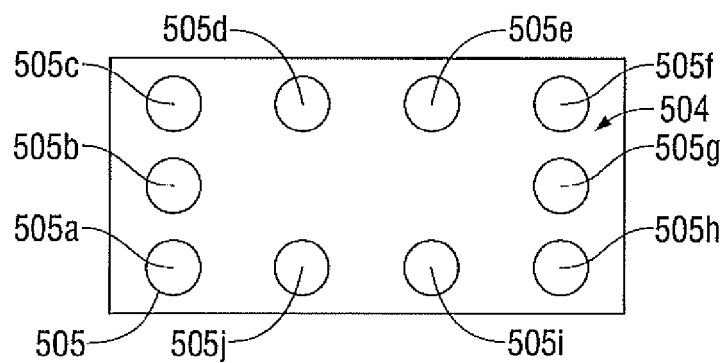
FIG. 8
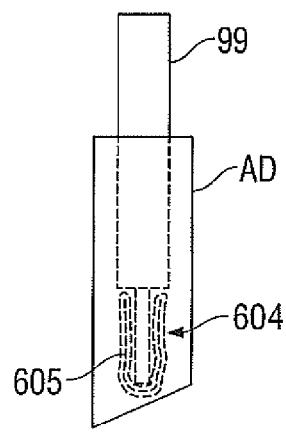 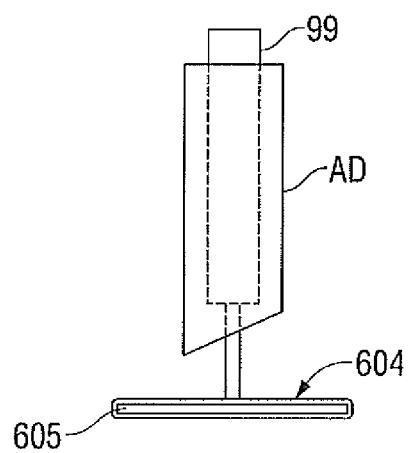
FIG. 9A   FIG. 9B

HERNIA REPAIR SYSTEM

BACKGROUND

1. Technical Field

The present disclosure relates to methods and systems for the application of a surgical mesh. More particularly, the present disclosure relates to systems and methods for anchoring a hernia mesh during minimally invasive surgery.

2. Description of Related Art

A hernia is a protrusion of a tissue, structure, or part of an organ through injured muscle tissue or an injured membrane by which the tissue, structure, or organ is normally contained. Some examples of hernias include: abdominal hernias, diaphragmatic hernias and hiatal hernias (for example, paraesophageal hernia of the stomach), pelvic hernias, for example, obturator hernia, anal hernias, hernias of the nucleus pulposus of the intervertebral discs, intracranial hernias, and Spigelian hernias.

Hernias may be surgically repaired, and are principally repaired by pushing back, or "reducing", the herniated tissue, and then reinforcing the defect in injured muscle tissue (an operation called herniorrhaphy). Modern muscle reinforcement techniques involve placement of an implant, such as a surgical mesh, near the injured tissue or defect to support the defect. The implant is either placed over the defect (anterior repair) or more often under the defect (posterior repair).

A variety of different fixation devices are used to anchor the implant into the tissue. For example, a needled suture may be passed through or around the tissue near the defect to hold the implant in a position which spans the injured tissue. In other examples, staples, tacks, clips and pins are also known to be passed through or around the tissue near the defect to anchor the implant in a position which spans the injured tissue. Although such methods have been proven effective in anchoring the implant into the tissue, penetration of the tissue by such devices may inflict addition trauma to the defect or the tissue near the defect and requires additional time for healing of the tissue.

SUMMARY

Accordingly, a hernia repair system includes a surgical mesh, one or more electrosurgical instruments, and one or more return electrodes. The one or more electrosurgical instruments and the one or more return electrodes are configured to selectively apply an effective amount of pressure and electrosurgical energy to the surgical mesh such that upon application of electrosurgical energy and pressure the surgical mesh seals to one side of tissue at the underlying tissue site. The surgical mesh may be bioabsorbable. The surgical mesh may include a bioactive agent. The surgical mesh may be partially or wholly formed of collagen. The one or more return electrodes are positionable adjacent the tissue externally relative to the underlying tissue site.

The one or more electrosurgical instruments are configured to position the surgical mesh adjacent tissue in an underlying tissue site. The one or more electrosurgical instruments include one or more jaws configured to position the surgical mesh adjacent tissue in the underlying tissue site. The one or more electrosurgical instruments may be configured to provide magnetized pressure between the one or more return electrodes and the one or more electrosurgical instruments. One or both of the one or more return electrodes and the one or more electrosurgical instruments may be operably connected to an electrosurgical energy source.

In embodiments, the hernia repair system may include a sensor operably associated with the at least one electrosurgical instrument and configured to detect one or both of pressure and energy. The sensor may be configured to collect one or both pressure and energy data as well as provide feedback based on the data.

In one aspect, a hernia repair system includes a surgical mesh and one or more electrosurgical instruments. The surgical mesh includes one or more electrodes embedded therein. The one or more electrodes may be weight or impedance dependant. The one or more electrodes may be expandable. A plurality of electrodes may be disposed around the perimeter of the surgical mesh.

The one or more electrosurgical instruments are configured to position the surgical mesh adjacent tissue in an underlying tissue site. The one or more electrosurgical instruments are configured to selectively apply an effective amount of pressure and electrosurgical energy to the one or more electrodes embedded in the surgical mesh such that upon the application of electrosurgical energy and pressure the surgical mesh seals to one side of the tissue at the underlying tissue site.

In one aspect, a method of attaching a surgical mesh includes providing a surgical mesh and one or more return electrodes. The method includes positioning the surgical mesh adjacent tissue in an underlying tissue site; positioning the one or more return electrodes adjacent the tissue externally relative to the underlying tissue site; applying an effective amount of pressure and electrosurgical energy to the surgical mesh; and sealing the surgical mesh on one side of the tissue at the underlying tissue site. The method may include the step of magnetically coupling the surgical mesh and the return electrode to create the effective amount of pressure to seal the surgical mesh to the tissue. One step may include affixing one or more electrodes to the surgical mesh such that upon activation of the one or more electrodes, the surgical mesh engages and seals to tissue in the underlying tissue site.

BRIEF DESCRIPTION OF THE DRAWINGS

The above and other aspects, features, and advantages of the present disclosure will become more apparent in light of the following detailed description when taken in conjunction with the accompanying drawings in which:

FIG. 7 is a top view of a further embodiment of a surgical mesh in accordance with the present disclosure;

FIG. 8 is a top view of one embodiment of a surgical mesh in accordance with the present disclosure;

FIG. 9A is a side view of one embodiment of a hernia repair system including a trocar, an electrosurgical instrument, and an embodiment of a surgical mesh, the hernia repair system in a first orientation; and FIG. 9B is a side view of the hernia repair system of FIG. 9A in a second orientation.

DETAILED DESCRIPTION

Figure 1A:
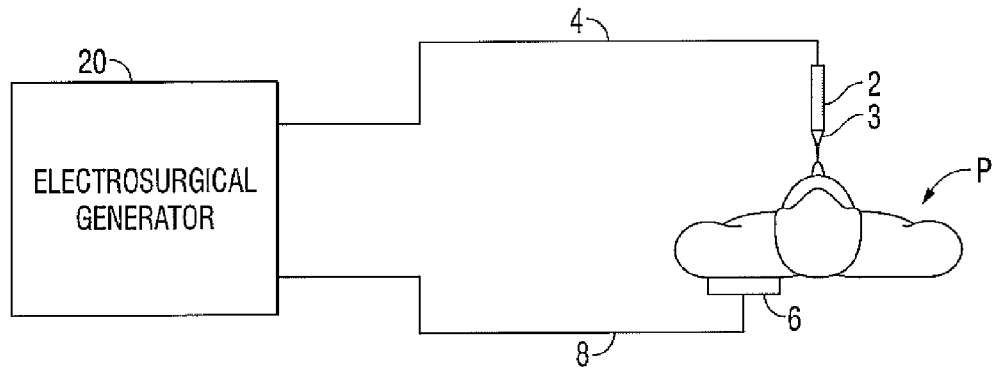
FIG. 1A is a schematic block diagram of a monopolar electrosurgical system according to an embodiment of the present disclosure.

The present disclosure relates to devices, systems, and methods for minimally invasive surgeries such as, endoscopic, laparoscopic, arthroscopic, endoluminal and/or transluminal placement of a surgical patch at a surgical site. As used herein the term "surgical mesh" is used to refer to any type of patch for use in surgical procedures, such as, for example, meshes that can be attached to the abdominal wall. Although described herein with reference to a hernia mesh, the method of the disclosure may be used in any surgical repair. As used herein the term "laparoscopic deployment device" is used to refer to a deployment device that may be used during minimally invasive surgeries described above.

In the drawings and in the description that follows, the term "proximal," as is traditional, will refer to an end of a device that is closer to the user, while the term "distal" will refer to the end of the device that is farther from the user.

Laparoscopic surgical procedures are minimally invasive procedures that are carried out within the body cavity through use of access ports in conjunction with elongated surgical devices. An initial opening in the body tissue enables passage of the endoscopic or laparoscopic device to the interior of the body. Openings include natural passageways of the body or openings that are created by a tissue piercing device such as a trocar. During laparoscopic procedures, narrow punctures or incisions are made minimizing trauma to the body cavity and reducing patient recovery time. Although described herein with reference to laparoscopic surgery, the method may be applied to any type of surgery.

Referring now in specific detail to the drawings, in which like numbers identify similar or identical elements, FIG. 1A is a schematic illustration of a monopolar electrosurgical system according to one embodiment of the present disclosure. The system includes a monopolar electrosurgical instrument 2 including one or more active electrodes 3. Electrosurgical RF energy is supplied to the instrument 2 by a generator 20 via a supply line 4 that is connected to an active terminal 30 (FIG. 2) of the generator 20. The generator 20 may include a plurality of outputs for interfacing with various electrosurgical instruments 2 (e.g., a monopolar active electrode, return electrode, bipolar electrosurgical forceps, footswitch, etc.). Further, the generator 20 includes electronic circuitry configured for generating radio frequency power specifically suited for various electrosurgical modes and procedures.

The energy is returned to the generator 20 through a return electrode 6 via a return line 8 at a return terminal 32 (FIG. 2) of the generator 20. The active terminal 30 and the return terminal 32 are connectors configured to interface with plugs (not explicitly shown) of the instrument 2 and the return electrode 6 that are disposed at the ends of the supply line 4 and the return line 8, respectively.

The system may include a plurality of return electrodes 6 that are arranged to minimize the chances of tissue damage by maximizing the overall contact area with the patient "P." In addition, the generator 20 and the return electrode 6 may be configured for monitoring so-called "tissue-to-patient" contact to ensure that sufficient contact exists therebetween to further minimize chances of tissue damage.

Not explicitly shown in FIG. 1A, the generator 20 includes suitable input controls (e.g., buttons, activators, switches, touch screen, etc.) for controlling the generator 20, as well as one or more display screens for providing the surgeon with variety of output information (e.g., intensity settings, treatment complete indicators, etc.). The controls allow the surgeon to adjust power of the RF energy, waveform, and other parameters to achieve the desired waveform suitable for a particular task. Further, the instrument 2 may include a plurality of input controls which may be redundant with certain input controls of the generator 20. Placing the input controls at the instrument 2 allows for easier and faster modification of RF energy parameters during the surgical procedure without requiring interaction with the generator 20.

Figure 1B:
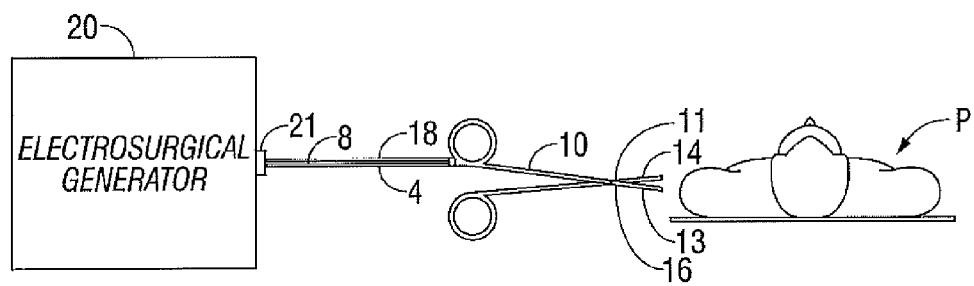
FIG. 1B is a schematic block diagram of a bipolar electrosurgical system in accordance with another embodiment of the present disclosure.
Figure 2:
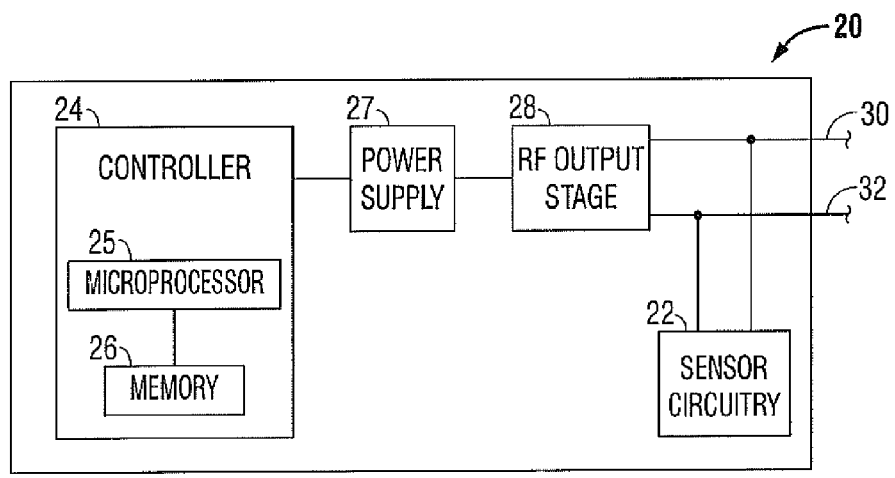
FIG. 2 is a schematic block diagram of a generator control system according to one embodiment of the present disclosure.

FIG. 1B is a schematic illustration of a bipolar electrosurgical system configured for use with the generator 20 according to the present disclosure. The system includes a bipolar electrosurgical forceps 10 having one or more electrodes for treating tissue of a patient "P." The electrosurgical forceps 10 includes opposing jaw members 11 and 13 having an active electrode 14 and a return electrode 16, respectively, disposed therein. The active electrode 14 and the return electrode 16 are connected to the generator 20 through cable 18, which includes supply and return lines 4, 8 coupled to the active and return terminals 30, 32, respectively (FIG. 2). The electrosurgical forceps 10 is coupled to the generator 20 via cable 18 at a connector 21 having connections (e.g., pins) to the active and return terminals 30 and 32. The connector 21 includes contacts from the supply and return lines 4, 8.

While the drawings depict an electrosurgical forceps 10 that is suitable for use in performing an open electrosurgical procedure, it is within the purview of the present disclosure that other types of electrosurgical forceps, e.g., electrosurgical forceps suitable for use in performing an endoscopic electrosurgical procedure, may be employed with the generator 20.

FIG. 2 shows a schematic block diagram of the generator 20 having a controller 24, a power supply 27, an RF output stage 28, and a sensor module 22. The power supply 27 may provide DC power to the RF output stage 28 which then converts the DC power into RF energy and delivers the RF energy to the instrument 2. The controller 24 includes a microprocessor 25 having a memory 26 which may be volatile type memory (e.g., RAM) and/or non-volatile type memory (e.g., flash media, disk media, etc.). The microprocessor 25 includes an output port connected to the power supply 27 and/or RF output stage 28 that allows the microprocessor 25 to control the output of the generator 20 according to either open and/or closed control loop schemes. One example of such an electrosurgical system is disclosed in U.S. patent application Ser. No. 12/351,935, filed Jan. 12, 2009, the content of which is incorporated in its entirety herein.

Figure 3A:
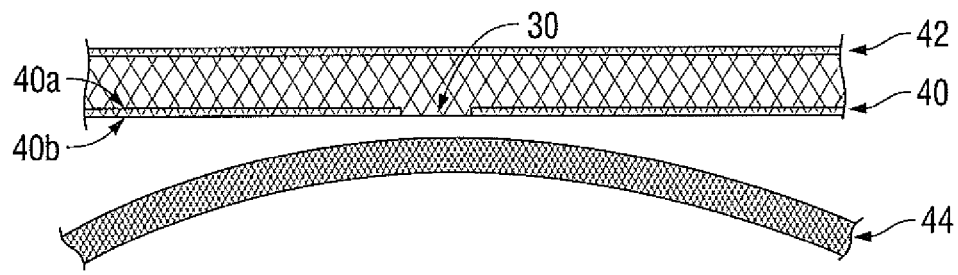
FIG. 3A is a schematic illustration of a tear in an abdominal wall.
Figure 3B:
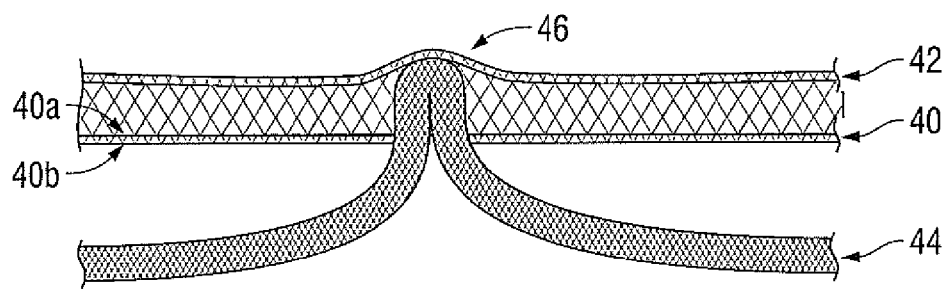
FIG. 3B is a schematic illustration of a ventral hernia.

A hernia may involve a tear 30 in the abdominal wall 40 as illustrated in FIG. 3A. The abdominal wall 40 is defined by an external side 40a and an internal side 40b. A surface tissue 42, which covers the external side 40a of abdominal wall 40, may or may not be immediately affected by this tear 30. An internal organ 44 located below the internal side 40b of the abdominal wall 40 may not protrude until some form of exertion or use of the muscle located at the abdominal wall 40 forces the internal organ 44 into the tear 30. Depending on the size and location of the tear 30, exertion may not be needed to cause the organ to protrude. As shown in FIG. 3B, a hernia occurs when an internal organ 44 protrudes into the tear 30 of abdominal wall 40. Oftentimes the protrusion creates a bulge 46 in the surface tissue 42.

Figure 4:
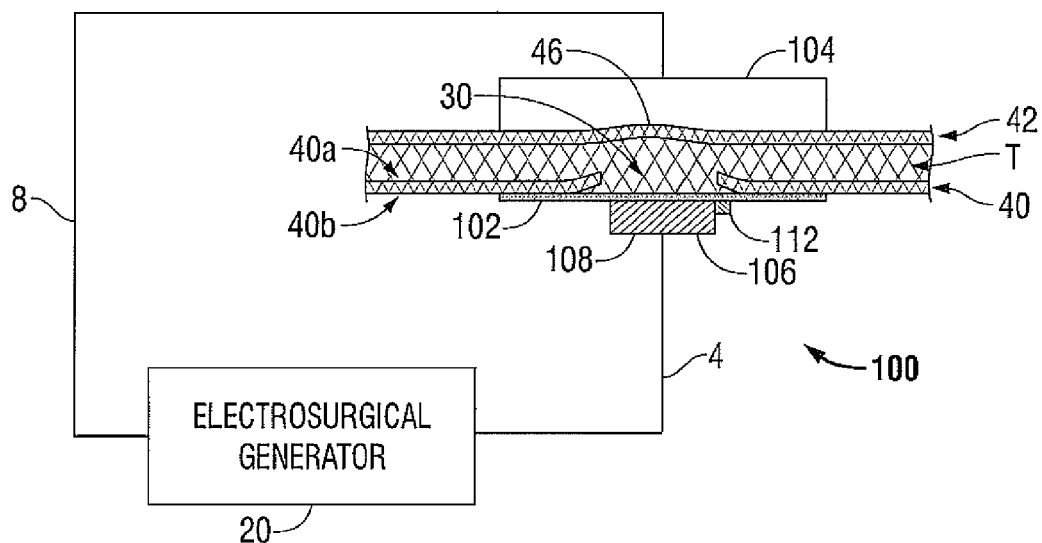
FIG. 4 is a schematic diagram of one embodiment of a hernia repair system including an electrosurgical return electrode, a surgical mesh, and an electrosurgical insertion instrument in accordance with the present disclosure.
Figure 5:
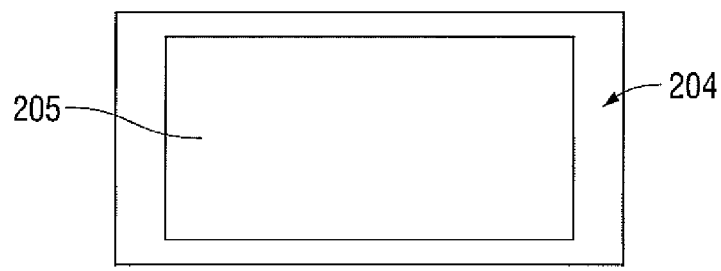
FIG. 5 is a top view of one embodiment of a surgical mesh in accordance with the present disclosure.
Figure 6:
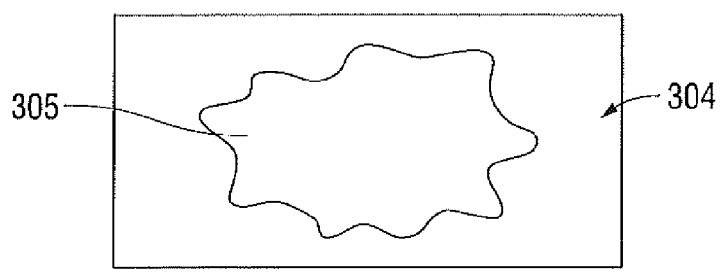
FIG. 6 is a top view of another embodiment of a surgical mesh in accordance with the present disclosure.

FIG. 4 illustrates an embodiment of a hernia repair system for performing a monopolar electrosurgical procedure on herniated tissue and is generally designated 100. The hernia repair system 100 includes a surgical mesh 102 (or plural surgical meshes 102), a return electrode 104 (or plural return electrodes 104), and an electrosurgical instrument 106 (or plural electrosurgical instruments 106). The electrosurgical instrument 106 and the return electrode 104 are configured to selectively apply an effective amount of energy (and possibly pressure) to the surgical mesh 102 such that the surgical mesh 102 is sealed on one side of tissue "T", in particular, the internal side 40b (e.g., the peritoneum) of the abdominal wall 40. In this manner, the electrosurgical instrument 106 provides a high current concentration and a high temperature so that the surgical mesh 102 seals on the internal peritoneum.

In some instances, it may be beneficial to use a bipolar forceps 10 (See FIG. 1B) to accomplish this purpose. In this embodiment, by controlling the electrosurgical energy delivered to the surgical site, the pressure (e.g., between about 3 kg/cm$^2$ to about 16 kg/cm$^2$), and the gap distance between opposing jaw members 11, 13 (e.g., between about 0.001 inches to about 0.006 inches), an effective seal may be formed. One example of such a forceps is disclosed in U.S. Pat. No. 7,160,299, the entire contents of which are incorporated herein by this reference.

The mesh 102 may be any type of mesh for use in surgical repair and suitable for use in situ. The mesh 102 may be any suitable shape (i.e., circular, noncircular, etc.) and may include one or more layers. The surgical mesh 102 may be made of multiple fibers, or may be made of a single fiber. The fibers may be a monofilament or multi-filament.

The fibers forming the mesh 102 may be made from a natural material or a synthetic material. The fibers may be biodegradable or non-biodegradable. It should be understood that any combination of natural, synthetic, bioadegradable and non-biodegradable materials may be used to form the fibers. The term "biodegradable" as used herein is defined to include both bioabsorbable and bioresorbable materials. By biodegradable, it is meant that the materials decompose, or lose structural integrity under body conditions (e.g. enzymatic degradation or hydrolysis) or are broken down (physically or chemically) under physiologic conditions in the body such that the degradation products are excretable or absorbable by the body.

Representative natural biodegradable polymers include: polysaccharides, such as alginate, dextran, chitin, hyaluronic acid, cellulose, collagen, gelatin, fucans, glycosaminoglycans, and chemical derivatives thereof (substitutions and/or additions of chemical groups, for example, alkyl, alkylene, hydroxylations, oxidations, and other modifications routinely made by those skilled in the art); and proteins, such as albumin, casein, zein, silk, and copolymers and blends thereof, alone or in combination with synthetic polymers.

Synthetically modified natural polymers include cellulose derivatives, such as alkyl celluloses, hydroxyalkyl celluloses, cellulose ethers, cellulose esters, nitrocelluloses, and chitosan. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, and cellulose sulfate sodium salt. These are collectively referred to herein as "celluloses."

Representative synthetic degradable polymers include polyhydroxy acids prepared from lactone monomers, such as glycolide, lactide, caprolactone, ε-caprolactone, valerolactone, and δ-valerolactone, as well as pluronics, carbonates (e.g., trimethylene carbonate, tetramethylene carbonate, and the like), dioxanones (e.g., 1,4-dioxanone and p-dioxanone), 1,dioxepanones (e.g., 1,4-dioxepan-2-one and 1,5-dioxepan-2-one), and combinations thereof. Polymers formed therefrom include: polylactides; poly(lactic acid); polyglycolides; poly(glycolic acid); poly(trimethylene carbonate); poly(dioxanone); poly(hydroxybutyric acid); poly(hydroxyvaleric acid); poly(lactide-co-(ε-caprolactone-)); poly(glycolide-co-(ε-caprolactone)); polycarbonates; poly(pseudo amino acids); poly(amino acids); poly(hydroxyalkanoate)s; polyalkylene oxalates; polyoxaesters; polyanhydrides; polyortho esters; and copolymers, block copolymers, homopolymers, blends, and combinations thereof.

Some non-limiting examples of suitable non-bioabsorbable materials from which the fibers may be made include: polyolefins, such as polyethylene and polypropylene including atactic, isotactic, syndiotactic, and blends thereof; polyethylene glycols; polyethylene oxides; ultra high molecular weight polyethylene; copolymers of polyethylene and polypropylene; polyisobutylene and ethylene-alpha olefin copolymers; fluorinated polyolefins, such as fluoroethylenes, fluoropropylenes, fluoroPEGSs, and polytetrafluoroethylene; polyamides, such as nylon and polycaprolactam; polyamines; polyimines; polyesters, such as polyethylene terephthalate and polybutylene terephthalate; aliphatic polyesters; polyethers; polyether-esters, such as polybutester; polytetramethylene ether glycol; 1,4-butanediol; polyurethanes; acrylic polymers and copolymers; modacrylics; vinyl halide polymers and copolymers, such as polyvinyl chloride; polyvinyl alcohols; polyvinyl ethers, such as polyvinyl methyl ether; polyvinylidene halides, such as polyvinylidene fluoride and polyvinylidene chloride; polyacrylonitrile; polyaryletherketones; polyvinyl ketones; polyvinyl aromatics, such as polystyrene; polyvinyl esters, such as polyvinyl acetate; copolymers of vinyl monomers with each other and olefins, such as etheylene-methyl methacrylate copolymers, acrylonitrile-styrene copolymers, ABS resins, and ethylene-vinyl acetate copolymers; alkyd resins; polycarbonates; polyoxymethylenes; polyphosphazine; polyimides; epoxy resins; aramids, rayon; rayon-triacetate; spandex; silicones; and combinations thereof.

The mesh 102 may be formed using any method suitable to forming mesh structures, including but not limited to knitting, weaving, non-woven techniques, and the like. Suitable techniques for making the mesh 102 are within the purview of those skilled in the art.

The mesh 102 may be any shape or size suitable for covering the herniated area and securing the mesh 102 to surrounding tissue. The mesh 102 may be preformed to a certain size, such as, for example, a 9 cm diameter round mesh or 50 cm×50 cm square mesh. In embodiments, the mesh 102 may be cut to a particular size and shape as needed.

The mesh 102 may include a bioactive agent. The term "bioactive agent", as used herein, is used in its broadest sense and includes any substance or mixture of substances that have clinical use. Consequently, bioactive agents may or may not have pharmacological activity per se, e.g., a dye. Alternatively a bioactive agent could be any agent that provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. It is envisioned that the bioactive agent may be applied to the mesh in any suitable form, e.g., films, powders, liquids, gels, and the like.

Examples of classes of bioactive agents, which may be utilized in accordance with the present disclosure include: anti-adhesives; antimicrobials; analgesics; antipyretics; anesthetics; antiepileptics; antihistamines; anti-inflammatories; cardiovascular drugs; diagnostic agents; sympathomimetics; cholinomimetics; antimuscarinics; antispasmodics; hormones; growth factors; muscle relaxants; adrenergic neuron blockers; antineoplastics; immunogenic agents; immunosuppressants; gastrointestinal drugs; diuretics; steroids; lipids; lipopolysaccharides; polysaccharides; platelet activating drugs; clotting factors; and enzymes. It is also intended that combinations of bioactive agents may be used.

Anti-adhesive agents can be used to prevent adhesions from forming between the mesh and the surrounding tissues opposite the target tissue. In addition, anti-adhesive agents may be used to prevent adhesions from forming between the coated implantable medical device and the packaging material. Some examples of these agents include, but are not limited to hydrophilic polymers such as polyvinyl pyrrolidone), carboxymethyl cellulose, hyaluronic acid, polyethylene oxide, poly vinyl alcohols, and combinations thereof.

Suitable antimicrobial agents which may be included as a bioactive agent include: triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine; polymyxin, tetracycline; aminoglycosides, such as tobramycin and gentamicin; rifampicin; bacitracin; neomycin; chloramphenicol; miconazole; quinolones such as oxolinic acid, norfloxacin, nalidixic acid, pefloxacin, enoxacin and ciprofloxacin; penicillins such as oxacillin and pipracil, nonoxynol 9, fusidic acid, cephalosporins; and combinations thereof. In addition, antimicrobial proteins and peptides such as bovine lactoferrin and lactoferricin B may be included as a bioactive agent.

Other bioactive agents, which may be included as a bioactive agent include local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g., oxybutynin); antitussives; bronchodilators; cardiovascular agents, such as coronary vasodilators and nitroglycerin; alkaloids; analgesics; narcotics such as codeine, dihydrocodeinone, meperidine, morphine and the like; non-narcotics, such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents, such as hormonal agents, hydrocortisone, prednisolone, prednisone, non-hormonal agents, allopurinol, indomethacin, phenylbutazone and the like; prostaglandins and cytotoxic drugs; chemotherapeutics, estrogens; antibacterials; antibiotics; anti-fungals; anti-virals; anticoagulants; anticonvulsants; antidepressants; antihistamines; and immunological agents.

Other examples of suitable bioactive agents, which may be included in the mesh include: viruses and cells; peptides, polypeptides and proteins, as well as analogs, muteins, and active fragments thereof; immunoglobulins; antibodies; cytokines (e.g., lymphokines, monokines, chemokines); blood clotting factors; hemopoietic factors; interleukins (IL-2, IL-3, IL-4, IL-6); interferons (β-IFN, α-IFN and γ-IFN); erythropoietin; nucleases; tumor necrosis factor; colony stimulating factors (e.g., GCSF, GM-CSF, MCSF); insulin; anti-tumor agents and tumor suppressors; blood proteins such as fibrin, thrombin, fibrinogen, synthetic thrombin, synthetic fibrin, synthetic fibrinogen; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); bone morphogenic proteins; TGF-B; protein inhibitors; protein antagonists; protein agonists; nucleic acids, such as antisense molecules, DNA, RNA, RNAi; oligonucleotides; polynucleotides; and ribozymes.

During laparoscopic surgery, the mesh 102 may be rolled, folded, or otherwise oriented so that the mesh 102 forms a shape more appropriate for transfer through any suitable laparoscopic device known in the art.

Referring again to FIG. 4, the electrosurgical instrument 106 includes one or more jaw members 108 configured to position the surgical mesh 102 adjacent tissue "T" in the underlying tissue site so that the electrosurgical instrument 106 and the return electrode 104 can apply RF energy to the surgical mesh 102. The amount of RF energy (and/or pressure) applied can be varied to accommodate the various materials and/or sizes of the surgical mesh 102 and/or the type and/or amount of tissue to which the surgical mesh 102 is being fused. One or both of the return electrode 104 and the electrosurgical instrument 106 may be operably connected to an electrosurgical energy source, such as the electrosurgical generator 20 discussed hereinabove.

Figure 3C:
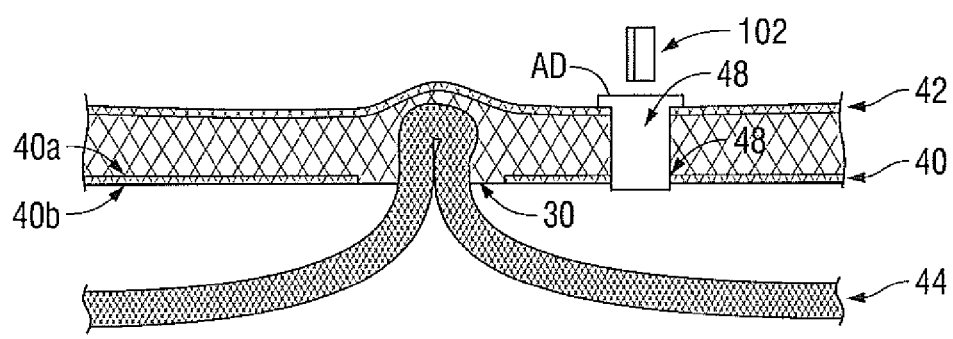
FIG. 3C is a schematic illustration of an incision and laparoscopic transfer of an embodiment of a surgical mesh in accordance with the present disclosure.
Figure 3D:
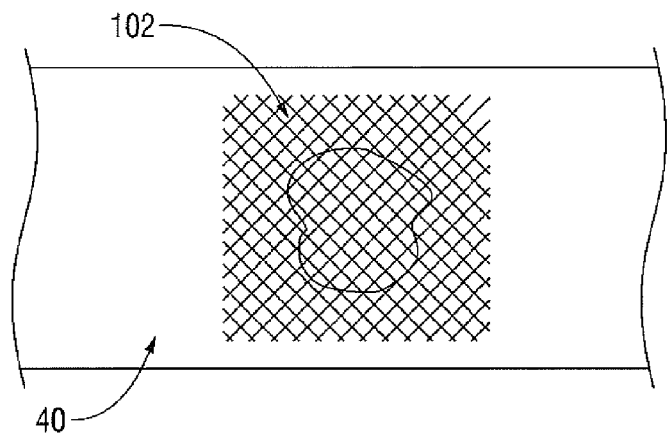
FIG. 3D is a schematic illustration of an abdominal wall during repair with the surgical mesh of FIG. 3C.
Figure 3E:
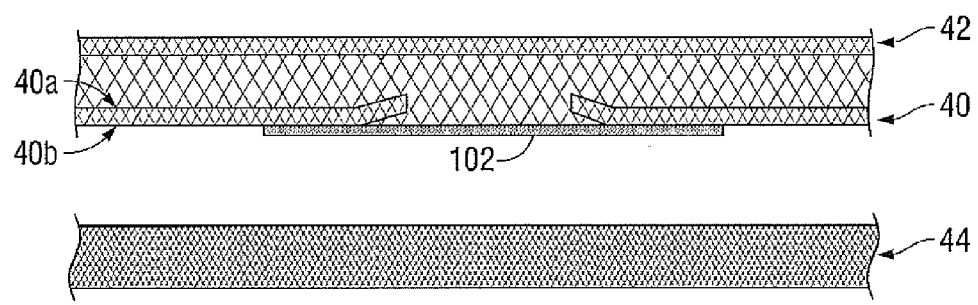
FIG. 3E is a schematic illustration of a tear in an abdominal wall following repair with the surgical mesh of FIGS. 3C and 3D.

As depicted in FIG. 3C, in order to correct the herniated tissue, an incision 48 may be made through the abdominal wall 40 in close proximity to the tear 30 and the mesh 102 may be inserted using a trocar/access device "AD" or similar laparoscopic device. As shown in FIG. 3D, the mesh 102 is then placed under the tear 30 on peritoneum 40b of the abdominal wall 40 with the electrosurgical instrument 106. The return electrode 104 is positioned adjacent the tissue "T" of the abdominal wall 40 (e.g., on the surface tissue 42) and externally of the underlying tissue site (FIG. 4). An effective amount of energy (and pressure in the case of bipolar) is applied to the mesh 102, sealing the mesh 102 on one side of the abdominal wall 40, namely the internal tissue 40b (e.g., the peritoneum) (FIG. 3D). Thus, the abdominal wall 40 is sealed, the protrusion 46 is repaired, and the internal organ 44 is returned to its original location (FIG. 3E).

The hernia repair system 100 may include a sensor 112 (FIG. 4) operably associated with the electrosurgical instrument 106. In embodiments, the sensor 112 may be mounted to the jaw 108 of the electrosurgical instrument 106. The sensor 112 may be configured to detect one or both of pressure and energy. The sensor 112 may be configured to collect one or both pressure and energy data as well as provide feedback (e.g., through the generator 20) based on the data.

Referring now to FIGS. 5-8, embodiments of surgical meshes 204, 304, 404, 504 each include one or more electrodes 205, 305, 405, 505 embedded therein. Each electrode 205, 305, 405, 505 may be one or both weight or impedance dependant. In particular, each electrode may be any suitable shape (e.g., circular or noncircular) including, but not limited to, square (FIG. 5), curvilinear (FIG. 6), or circular (FIG. 7). As best shown in FIG. 8, a plurality of electrodes 505a-505j may be disposed around the perimeter of one embodiment of a surgical mesh 504. In this embodiment, each electrode 505a-505j can be activated individually, in combination with some of the other electrodes, and/or simultaneously with all other electrodes. Upon activation of the one or more electrodes 505a-505j, the surgical mesh 504 sealingly engages tissue "T" in the underlying tissue site.

In some embodiments, the electrosurgical instrument 106 is magnetized and may be configured to provide magnetized pressure between the return electrode 104 and the electrosurgical instrument 106 such that the tissue "T" and the mesh 102 approximate or otherwise converge. In addition, the electrosurgical instrument 106 may locate the mesh 102 by the application of magnetism when the electrosurgical instrument 106 is positioned externally of a patient's body.

In one embodiment of a surgical mesh 604, illustrated in FIGS. 9A-9B, the surgical mesh 604 includes an expandable electrode 605. In this embodiment, the electrode 605 is positionable between an unexpanded condition (FIG. 9A) so that the surgical mesh 604 can be readily passed through the access device "AD", and an expanded condition (FIG. 9B) for readily positioning the surgical mesh 604 adjacent tissue "T", namely the herniated tissue, in an underlying tissue site.

After placement of one or more of the surgical meshes 204, 304, 404, 504, 604, an electrosurgical instrument 99 selectively applies an effective amount of energy (and pressure in the case of bipolar) to the respective electrodes 205, 305, 405, 505, 605 embedded in the one or more surgical meshes 204, 304, 404, 504, 604 such that the one or more surgical meshes 204, 304, 404, 504, 604 are sealed on the internal side 40b of the tissue "T" of the abdominal wall 40.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A hernia repair system, comprising:
   a surgical mesh;
   an electrosurgical instrument configured to position the surgical mesh adjacent tissue in an underlying tissue site and to provide a magnetic force that converges the surgical mesh to the tissue; and
   at least one return electrode positionable adjacent the tissue externally relative to the underlying tissue site;
   wherein the electrosurgical instrument and the at least one return electrode are configured to selectively apply an effective amount of electrosurgical energy to the surgical mesh such that upon application of electrosurgical energy, the surgical mesh seals to one side of the tissue at the underlying tissue site.

2. The hernia repair system of claim 1, wherein the surgical mesh is formed at least partially of collagen.

3. The hernia repair system of claim 1, wherein the electrosurgical instrument includes at least one jaw configured to position the surgical mesh adjacent tissue in the underlying tissue site.

4. The hernia repair system of claim 3, further comprising a sensor operably associated with the electrosurgical instrument and configured to detect at least one of pressure and energy.

5. The hernia repair system of claim 4, wherein the sensor is configured to collect at least one of pressure and energy data and provide feedback based on the data.

6. The hernia repair system of claim 4, wherein the sensor is mounted on the at least one jaw.

7. The hernia repair system of claim 1, wherein at least one of the at least one return electrode and the electrosurgical instrument is operably connected to an electrosurgical energy source.

8. The hernia repair system of claim 1, wherein the surgical mesh is bioabsorbable.

9. The hernia repair system of claim 1, wherein the surgical mesh includes a bioactive agent.

10. The hernia repair system of claim 1, wherein the surgical mesh is formed of a material that enables the electrosurgical instrument to apply magnetic forces to the surgical mesh.

11. The hernia repair system of claim 10, wherein the electrosurgical instrument is configured to locate the surgical mesh from a position external of the underlying tissue site upon the application of magnetic forces.

12. The hernia repair system of claim 1, wherein the electrosurgical instrument includes a plurality of jaw members.

13. A hernia repair system, comprising:
   a surgical mesh;
   a magnetized electrosurgical instrument that generates a magnetic force to converge a surgical mesh to tissue in an underlying tissue site and selectively applies an effective amount of electrosurgical energy to the surgical mesh to seal the surgical mesh to the tissue at the underlying tissue site.

14. The hernia repair system of claim 13, wherein the surgical mesh is formed of a material that enables the electrosurgical instrument to apply magnetic forces to the surgical mesh.

* * * * *